US010274390B2

(12) United States Patent
Sieber et al.

(10) Patent No.: US 10,274,390 B2
(45) Date of Patent: Apr. 30, 2019

(54) TANK PRESSURE TRANSMITTER WITH INTEGRATED BREATHING GAS ANALYZER

(71) Applicants: Arne Sieber, Graz (AT); Reima K. Holopainen, Zufikon (CH); Joe Stella, Ipswich, MA (US); Sebastian Reif, Graz (AT); Bradley E. Lally, San Diego, CA (US)

(72) Inventors: Arne Sieber, Graz (AT); Reima K. Holopainen, Zufikon (CH); Joe Stella, Ipswich, MA (US); Sebastian Reif, Graz (AT); Bradley E. Lally, San Diego, CA (US)

(73) Assignee: Johnson Outdoors Inc., Racine, WI (US)

( * ) Notice: Subject to any disclaimer, the term of this patent is extended or adjusted under 35 U.S.C. 154(b) by 148 days.

(21) Appl. No.: 15/404,464

(22) Filed: Jan. 12, 2017

(65) Prior Publication Data
US 2018/0195923 A1    Jul. 12, 2018

(51) Int. Cl.
| | | |
|---|---|---|
| *G01L 19/08* | (2006.01) | |
| *G01N 33/00* | (2006.01) | |
| *B63C 11/02* | (2006.01) | |
| *B63C 11/18* | (2006.01) | |

(52) U.S. Cl.
CPC ......... *G01L 19/086* (2013.01); *G01N 33/004* (2013.01); *G01N 33/0036* (2013.01); *B63C 11/02* (2013.01); *B63C 2011/021* (2013.01); *B63C 2011/188* (2013.01)

(58) Field of Classification Search
CPC .......... G01L 19/086; G01N 33/0036; G01N 33/004; G01N 33/0016; G01N 7/00; B63C 2011/188; B63C 2011/021; B63C 11/02; B63C 11/18
See application file for complete search history.

(56) References Cited

U.S. PATENT DOCUMENTS

| | | |
|---|---|---|
| 4,173,975 A | 11/1979 | DeLong et al. |
| 4,876,903 A | 10/1989 | Budinger |
| 5,738,092 A | 4/1998 | Mock et al. |
| 5,806,514 A | 9/1998 | Mock et al. |

(Continued)

FOREIGN PATENT DOCUMENTS

| | | |
|---|---|---|
| EP | 0274868 A1 | 7/1988 |
| WO | WO 95/08471 A1 | 3/1995 |

(Continued)

OTHER PUBLICATIONS

Robert N. Rossier; When Gas Goes Bad; publication online; Fall 2010; 4 pages; http://www.alertdiver.com/402.

(Continued)

*Primary Examiner* — Blake A Tankersley
(74) *Attorney, Agent, or Firm* — Reinhart Boerner Van Deuren P.C.

(57) ABSTRACT

A tank pressure transmitter with integrated breathing gas analyzer and associated methods are provided. The tank pressure transmitter can include a gas sensor which detects a constituent of a breathing gas. The transmitter is operable to compile a constituent reading from the constituent detected, and communicate this constituent reading wirelessly to a dive computer.

11 Claims, 9 Drawing Sheets

(56) References Cited

U.S. PATENT DOCUMENTS

| | | | |
|---|---|---|---|
| 6,360,182 B1* | 3/2002 | Hales | A62B 18/08 |
| | | | 128/201.27 |
| 8,275,311 B2 | 9/2012 | Lindman | |
| 2004/0046710 A1 | 3/2004 | Adams et al. | |
| 2005/0109133 A1 | 5/2005 | Lamb | |
| 2011/0041848 A1 | 2/2011 | Stone et al. | |
| 2016/0238494 A1* | 8/2016 | Chrin, II | G01N 1/2247 |
| 2017/0050711 A1* | 2/2017 | Kerr | A61G 10/026 |

FOREIGN PATENT DOCUMENTS

| | | |
|---|---|---|
| WO | WO 2014/099991 A1 | 6/2014 |
| WO | WO 2015/166234 A1 | 11/2015 |

OTHER PUBLICATIONS

Daniele Zanoni; A little refresher on how to analyse your Nitrox tank properly; publication online; Feb. 9, 2009; 2 pages; http://www.emperordivers.com/blog/2009/02/a-little-refresher-on-how-to-a.html.

* cited by examiner

TANK PRESSURE TRANSMITTER WITH INTEGRATED BREATHING GAS ANALYZER

FIELD OF THE INVENTION

This invention generally relates to diving devices, and more particularly to devices associated with providing a breathing gas to a diver from an associated tank.

BACKGROUND OF THE INVENTION

Nitrox mixtures are a popular form of oxygen enriched breathing gas used in diving applications. In its basic form, Nitrox is a mixture of oxygen ($O_2$) and nitrogen. Nitrox has the advantage of lengthening no-decompression limits, shortening surface intervals, and providing an added safety buffer for decompression sickness in certain circumstances.

Diving with nitrox, however, exposes the diver to higher partial pressures of oxygen ($PO_2$) during a dive, even at recreational depths. Considering a maximum recreational depth of 40 meters and a nitrox mixture of 40% oxygen, the partial pressure of oxygen is 1.6 bar at 30 meters. Oxygen becomes toxic above 1.6 bar. Oxygen intoxication can lead to convulsions, which if they occur during a dive, can be fatal.

Nitrox is a prepared gas, and for safety reasons, the fraction or percentage of oxygen ($FO_2$) is written directly on the tank. This allows a diver to select the appropriate nitrox concentration when preparing for a dive. However, there is always a risk that tank may be improperly filled or improperly marked. As a result, divers must analyze the gas of their diving tank before a dive. In some countries it is mandatory for divers to conduct this analysis themselves and fill out a protocol. To conduct such an analysis, the diver uses a nitrox analyzer.

A typical nitrox analyzer is a separate device containing an oxygen sensor. In use, a diver decants gas from their tank and flushes the oxygen sensor of the nitrox analyzer with the decanted gas. The nitrox analyzer contains a display which then provides a reading of the fraction or percentage of oxygen.

While such nitrox analyzers provide a means for ascertaining $FO_2$, the above devices and process is now without its drawbacks. For example, analyzing nitrox is time consuming and requires a separate device, i.e. the above mentioned nitrox analyzer. Further, a user may incorrectly use the analyzer, resulting in an incorrect reading. Still further, after the analysis is completed, the information collected must be archived.

After correct analysis of the breathing gas, the diver has to enter the O2 fraction into the dive computer. This is required, so that the dive computer can correctly calculate the inert gas fraction of the breathing gas, and then correctly calculate inert-gas tissue loadings. This is a time consuming step. Moreover, this is also another failure source—if the diver makes a mistake by entering the incorrect O2 faction into the dive computer, the dive computer is unable to perform correct decompression calculations, which may lead to decompression sickness.

The above issues also persist for deeper diving applications which utilize other types of gases, such as those containing helium. In such applications, the gas must tested as in the above example pertaining to nitrox. This testing is done using a separate analyzer in a similar fashion as mentioned above. However, both helium and oxygen percentage levels must be tested which is even more time consuming. Further, such analyzers capable of analyzing helium as well are considerably costly.

It is also good practice to analyze breathing gases for contaminants prior to a dive. Such contaminants may include among others carbon monoxide (CO), carbon dioxide (CO2), oil, or water. Even small amounts of CO may lead to carbon monoxide poisoning, which may be fatal. Further, a high water content in the breathing gas may lead to freezing of the breathing regulator in cold-water diving, which is also problematic. Many breathing gas filling stations have sensors to continuously check the quality of the breathing gas, however there are also many filling stations who do not have such systems. The diver must resort to portable reusable or single use systems, similar to a nitrox analyzer described above.

Accordingly, there is a need in the art for a system for automatically analyzing the constituents of a breathing gas, so that possible user errors can be excluded and safety can be increased. It would also be highly advantageous if such a system also automatically communicates with a dive computer regarding the information collected so that minimal to no user intervention is required prior to a dive to reduce pre-dive preparation time. The invention provides such a system. These and other advantages of the invention, as well as additional inventive features, will be apparent from the description of the invention provided herein.

BRIEF SUMMARY OF THE INVENTION

In one aspect, the invention provides a wireless tank pressure transmitter. The embodiment of such a wireless tank pressure transmitter includes a housing having at least one inlet. The at least one inlet is operable to receive an inlet flow of breathing gas from a high pressure regulator. The wireless tank pressure transmitter also includes a pressure sensor disposed within the housing and connected to the at least one inlet. The pressure sensor is operable to detect a pressure of the breathing gas supplied through the at least one inlet. The wireless tank pressure transmitter also includes a gas sensor disposed within the housing and connected to the at least one inlet. The gas sensor is operable to detect a constituent of the breathing gas.

The wireless tank pressure transmitter also includes a control arrangement disposed within the housing and configured for compiling a pressure reading from the pressure taken by the pressure sensor and for compiling a constituent reading from the constituent taken by the gas sensor. The control arrangement is configured for wireless communication of the pressure reading and the constituent reading to a dive computer.

In certain embodiments, the gas sensor can be an oxygen sensor. The oxygen sensor may be among others an optical oxygen sensor, a galvanic oxygen sensor, a solid state ceramic oxygen sensor, and a paramagnetic oxygen sensor.

In certain embodiments, the gas sensor is disposed within a measurement chamber in communication with the at least one outlet. A flow orifice may be disposed upstream from the measurement chamber relative to a flow direction of the breathing gas. The flow orifice may be sized to reduce the inlet flow of the breathing gas to the measurement chamber. In a particular embodiment, the flow orifice is sized to reduce the inlet flow of the breathing gas to a flow rate of less than 0.1 standard liters per minute.

In certain embodiments, the measurement chamber may also include a vent for evacuating the breathing gas therefrom. A pressure regulator may be disposed upstream from the flow orifice relative to the flow direction of the breathing gas. The pressure regulator is operable to regulate the pressure of the inlet flow of breathing gas to the measurement chamber.

In certain embodiments, the constituent reading may be at least one of a fraction of oxygen in the breathing gas and a partial pressure of oxygen in the breathing gas. The gas sensor may also include multiple different gas sensors each of which configure to detect a different constituent from one another. The gas sensor may also be a helium sensor, carbon monoxide sensor, or other type of gas sensor.

In certain embodiments, the at least one inlet can include a high pressure inlet and an intermediate inlet. The high pressure inlet is connected to a high pressure outlet port of the first stage pressure regulator. The intermediate inlet is connected to an intermediate outlet port of the first stage pressure regulator. A first flow of the breathing gas from the high pressure inlet is provided to the pressure sensor. A second flow of the breathing gas from the intermediate inlet is provided to the gas sensor.

In another aspect, the invention provides a method for automatically analyzing breathing gas. An embodiment of such a method includes detecting a constituent of the breathing gas with a gas sensor disposed within a housing having at least one inlet. The at least one inlet is coupled to a first stage pressure regulator. The gas sensor is connected to the at least one inlet. This method also includes compiling a constituent reading from the constituent detected by the gas sensor via a control arrangement disposed within the housing and operably connected to the gas sensor. This method also includes wirelessly communicating the constituent reading to a dive computer.

The method may also include detecting a pressure of the breathing gas with a pressure sensor disposed within the housing. The pressure sensor is connected to the at least one inlet. According to this embodiment, the method may also include compiling a pressure reading from the pressure detected by the pressure sensor via the control arrangement. This embodiment of the method may also include wirelessly communicating a pressure reading to the dive computer.

In certain embodiments, the step of compiling a constituent reading includes compiling a partial pressure of the constituent. The method may also include wirelessly communicating the partial pressure reading to the dive computer. The method may also include determining, in the dive computer, a percentage of the gas constituent present in the breathing gas based on the partial pressure communicated.

In certain embodiments, the step of detecting a constituent includes detecting multiple different constituents. The step of compiling includes compiling a constituent reading for each of the multiple different constituents. The step of wirelessly communicating includes wirelessly communicating each constituent reading to a dive computer.

In certain embodiments, the method includes automatically determining decompression calculations in the dive computer based on the constituent readings wirelessly communicated. The method may also include providing an indication at the dive computer regarding the constituent reading. The indication may be at least one of a displayed message, an optical indication, and an audible indication.

Other aspects, objectives and advantages of the invention will become more apparent from the following detailed description when taken in conjunction with the accompanying drawings.

BRIEF DESCRIPTION OF THE DRAWINGS

The accompanying drawings incorporated in and forming a part of the specification illustrate several aspects of the present invention and, together with the description, serve to explain the principles of the invention. In the drawings.

While the invention will be described in connection with certain preferred embodiments, there is no intent to limit it to those embodiments. On the contrary, the intent is to cover all alternatives, modifications and equivalents as included within the spirit and scope of the invention as defined by the appended claims.

DETAILED DESCRIPTION OF THE INVENTION

Turning now to the drawings, FIGS. 1-9 illustrate several configurations of a tank pressure transmitter with integrated breathing gas analyzer 20 according to the teachings herein. As will be understood more fully below, a tank pressure transmitter with integrated breathing gas analyzer according to the teachings herein overcomes existing problems in the art by providing both tank pressure monitoring and breathing gas analysis in a single packaged unit. Even more advantageous, the data collected by the transmitter according to the teachings herein is wirelessly communicated to a dive computer. As a result, a diver no longer has to rely on a separate device to test the breathing gas, as this function is now performed in tandem with tank pressure monitoring using a common device automatically which also advantageously reduced or eliminates any user data entry errors. As a result, the dive computer can do fast and accurate calculations, e.g. decompression calculations.

Figure 1:
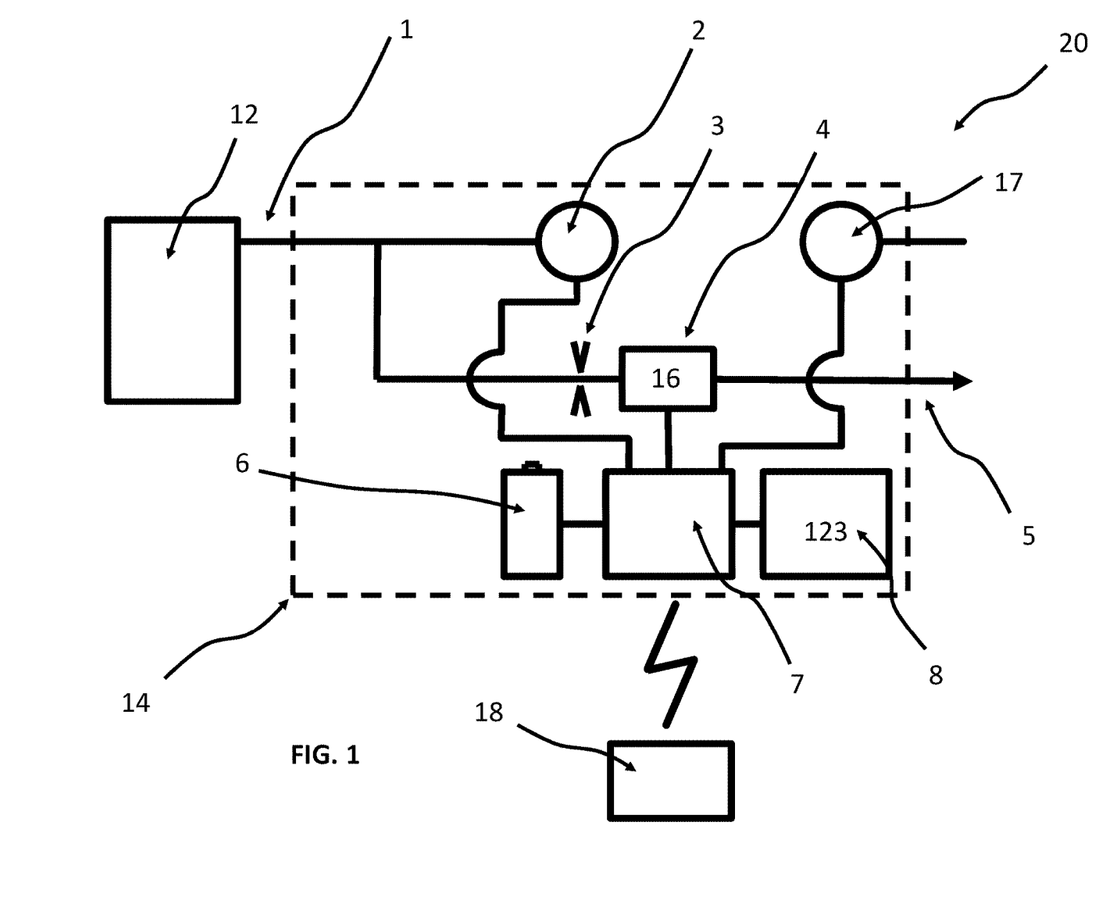
FIG. 1 is a schematic representation of one configuration of a tank pressure transmitter with integrated breathing gas analyzer according to the teachings herein.

Turning now to FIG. 1, the same schematically shows one configuration of a tank pressure transmitter with integrated breathing gas analyzer 20 (hereinafter "system"). System 20 includes a housing 14 which may be a multi-cavity or single-cavity housing. System 20 includes at least one inlet for receiving a breathing gas. In the illustrated configuration, system 20 includes a high pressure inlet 1 which is configured to receive a breathing gas via its connection to a high pressure port of a first stage pressure regulator 12 regulating the breathing gas. The first stage pressure regulator 12 may be any known first stage pressure regulator, and thus the invention is not limited to any particular type of first stage pressure regulator.

A pressure of the breathing gas is measured with a pressure sensor 2. This pressure sensor 2 is disposed within housing and is in communication with the high pressure inlet 1. Pressure sensor 2 may be configured to wake system 20 upon the detection of a sufficiently high pressure through high pressure inlet 1. Likewise, when the pressure detected by pressure sensor 2 falls below a certain threshold value, e.g. 10 bar, then the unit can enter sleep mode. In addition to being conveyed to pressure sensor 2, breathing is also conveyed from the high pressure inlet 1 to an orifice 3 which is used to generate a low gas flow to a measurement chamber 4. One or more gas sensors 16 are located in the measurement chamber 4.

Gas sensor(s) 16 is operable to sense one or more constituents of the breathing gas. As used herein, "constituent" broadly refers to any particular element, molecule, compound, contaminant or substance present in the breathing gas. For example, a constituent could the oxygen molecules ($O_2$) in the breathing gas. The constituent may also be other substances in the breathing gas or attributes of the breathing gas, such as CO, $CO_2$, He, water molecules or oils present in the breathing gas, humidity, etc. Accordingly, gas sensor 16 may take the form of any sensor necessary to collect the desired data, e.g. CO, $CO_2$, humidity, He, and/or oil sensors. The gas sensor 16 thus can take a variety of forms to perform a variety of sensing methods. As non-limiting examples, gas sensor 16 may employ electrochemical gas sensing, optical fluorescence gas sensing, paramagnetic based measurement, solid state sensing technology, etc.

Where oxygen is the particular constituent of interest, gas sensor 16 may for example be, among others, an optical oxygen sensor, a galvanic oxygen sensor, a solid state ceramic oxygen sensor, or a paramagnetic oxygen sensor. Accordingly, it is envisioned that multiple gas sensors 16 may be utilized simultaneously to collect various attributes of the breathing gas. Reference to a gas sensor 16 herein should thus be taken to mean one or more sensors.

After being decanted over sensor or sensors 16, the breathing gas is then vented to the environment through an exhaust outlet 5 formed in the measurement chamber 4. The signals of the gas sensor 16 and the pressure sensor 2 are processed by a control arrangement 7 in operable communication with gas sensor 16 and pressure sensor 2. This control arrangement 7 comprises a microcontroller or microprocessor and a wireless electromagnetic transmitter and any other componentry, firmware, software, etc. required to read and interpret the signals provided from gas sensor 16 and pressure sensor 2, optionally temporarily or permanently store information regarding these signals, and transmit such information by a wired or wireless connection to another device or display, as explained below.

Control arrangement 7 functions to compile the signals received by the gas sensor 16 and high pressure sensor 2 into a pressure reading based on the signal from pressure sensor 2 and a constituent reading based on the signal from the gas sensor 16. The pressure reading may be in the form of any conventional pressure data, and the constituent reading may be in the form of any conventional constituent data. As one example of such a constituent reading, in the case of oxygen as the constituent, the constituent reading may be a fraction or percentage of oxygen (FO2) in the breathing gas. Another constituent reading could be the partial pressure of the oxygen (PO2) in the breathing gas. Where partial pressure PO2 is determined, a subsequent determination of the fraction of oxygen FO2 may be done locally in system 20, and/or in a dive computer 18 based on other data collected such as ambient pressure. The ambient pressure information may be collected locally in system 20 using an ambient pressure sensor 17 in operable communication with control arrangement 7, and exposed to ambient pressure via a conduit through housing 14.

The pressure reading and constituent reading may then be communicated to a dive computer 18. As a particularly advantageous embodiment, these readings are communicated wirelessly to dive computer 18. Such wireless communications protocol may take the form of any wireless communications protocol typically used in diving applications. For example, the communication may be via a Bluetooth, wifi, or short range radio scheme at relatively shorter depths, while low frequency transmission, optical transmission, or data transmission via sound may be used at relatively deeper depths.

Further, diving computer 18 may take the form of any contemporary diving computer configured at least for wireless reception of information, and as such, is illustrated in non-limiting schematic form. The data provided to dive computer 18 may be utilized for additional functionality of the system as well. For example, based on the information provided by control arrangement 7, the dive computer 18 may provide a warning as a diver approaches or exceeds the MOD (maximum operating depth) for the gas used. Further, if the diver intends to use a gas switching procedure during the dive, dive computer 18 could also provide an indication that the wrong gas is being used. Yet further, dive computer may provide an indication of exceedingly high contaminant levels in the breathing gas. Without limitation by the preceding, dive computer 18 may provide an indication based on any of the information collected by system 20. Such an indication may be any one of a displayed reading or message, an optical indication, or an audible indication.

An optional display 8 may be incorporated into housing 14 to display the pressure reading and/or constituent reading. Display 8 may take the form of any display typically used for diving applications. A battery 6 is used as power supply. Battery 6 may take the form of any conventional battery. Those skilled in the art, however, will recognize that the particular display 8 and battery 6 will depend upon the intended application of the system herein. This additional display 8 has the added advantage of providing the above readings and information directly at system 20 as well as at the diving computer 18. Such a redundant communication is advantageous where wireless communication to dive computer 18 is unachievable due to local interference or the like.

On the surface, when the tank pressure valve is closed and there is no supply pressure through the first stage pressure regulator 12, there is no breathing gas flow through the orifice 3 and the measurement chamber 4, but the measurement chamber is connected through the exhaust outlet 5 to the environment. As a result of this exposure to the environment, and after some time, the gas fractions inside measurement chamber 4 will be equal to the gas fractions of the environment, which allows an auto-calibration of system 20, as the environment is typically air with known gas fractions. Accordingly, control arrangement 7 may thus also perform such an auto-calibration.

Figure 2:
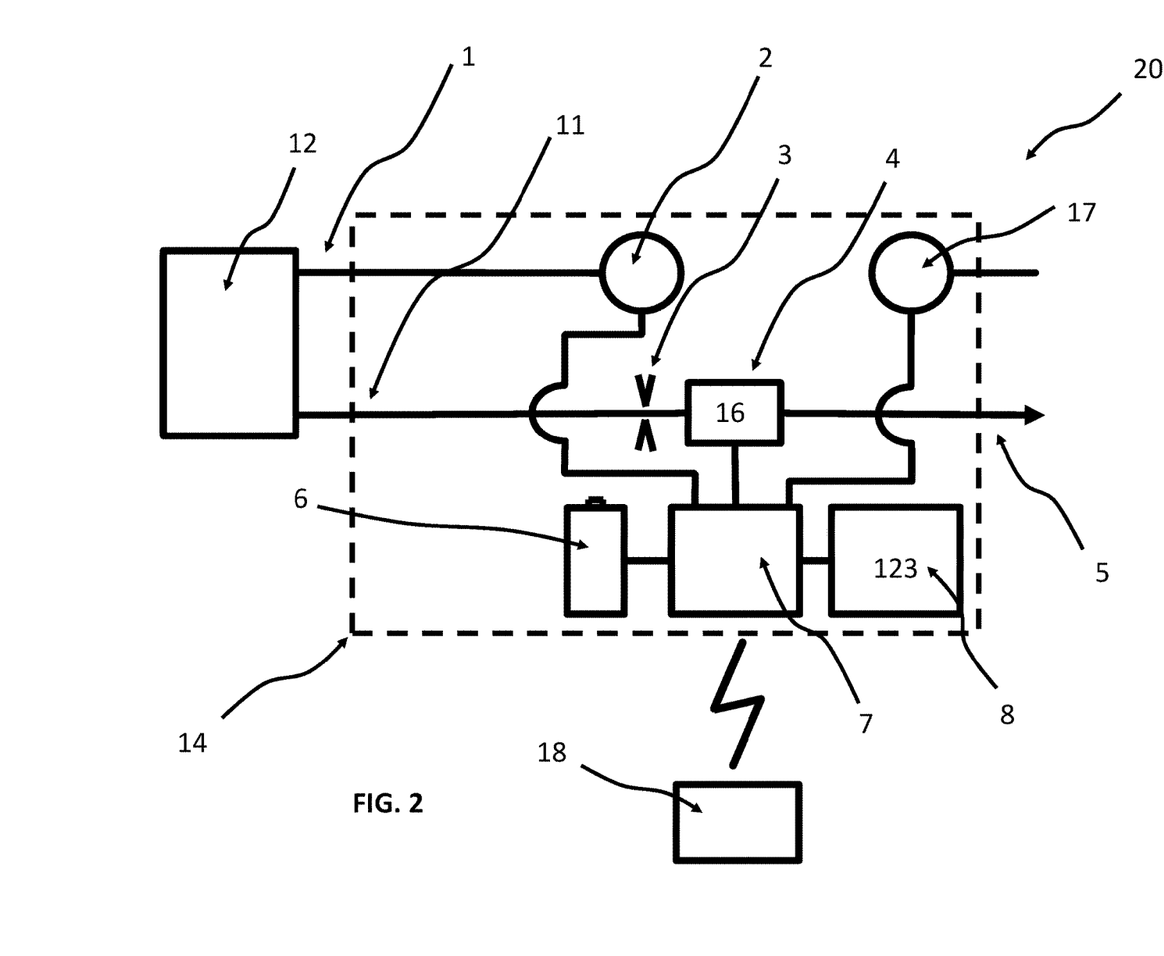
FIG. 2 is a schematic representation of an alternate configuration of the tank pressure transmitter with integrated breathing gas analyzer of FIG. 1.

Turning now to FIG. 2, the same illustrates another configuration of system 20 which employs a dual-inlet scheme. Indeed, with momentary reference back to FIG. 1, the same includes a single inlet 1 connected to the high pressure port of a first stage pressure regulator. The flow of breathing gas through measurement chamber 4 in the configuration of system 20 shown in FIG. 1 is dependent on the pressure of the supply of breathing gas. During a dive this supply pressure typically falls from 200-300 bar at the beginning of the dive to 50 bar or even less at the end of a dive. That means that the gas flow through orifice 3 would be up to 6 times higher at the beginning of the dive than at the end of the dive. FIG. 2 thus provides a more gas efficient version of system 20.

In the configuration of FIG. 2, inlet 1 remains connected to this high pressure port. However, an additional inlet 11 is provided which is connected to the intermediate pressure port of a first stage pressure regulator. As can be seen in FIG. 2, orifice 3 is supplied via inlet 11 with breathing gas from the intermediate pressure port of the first stage regulator. In diving systems this intermediate pressure is usually about 7-10 bar above ambient pressure, which allows a more constant gas flow. Moreover in such an arrangement it is possible to use a larger orifice, which is simpler and cheaper to manufacture and is less prone to clogging.

Figure 3:
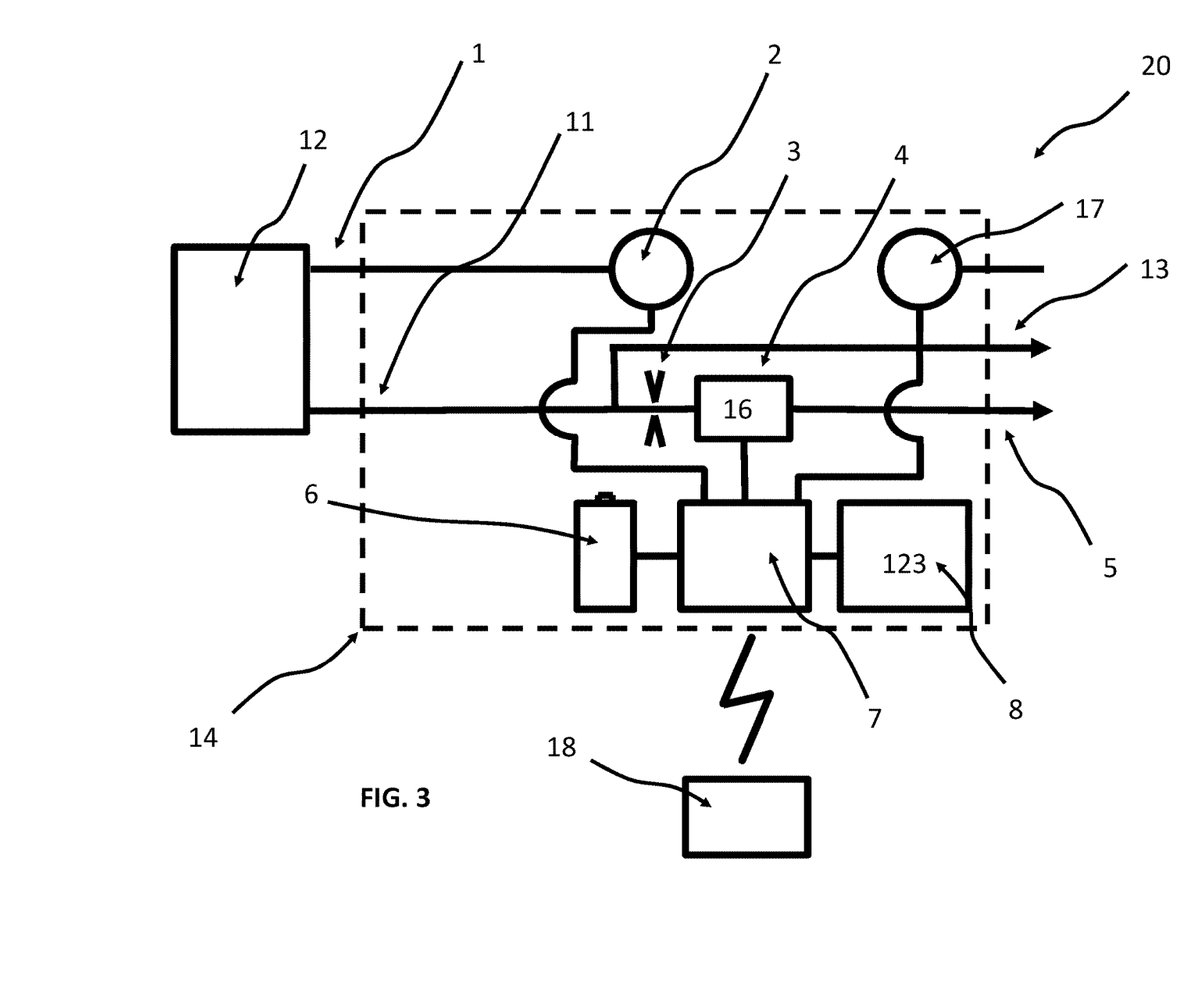
FIG. 3 is a schematic representation of an alternate configuration of the tank pressure transmitter with integrated breathing gas analyzer of FIG. 1.

As can be surmised from a comparison between FIGS. 1 and 2, the remainder of the configuration shown in FIG. 2 is identical to the configuration of FIG. 1. The configuration of FIG. 3 is identical to that of FIG. 2 except that it not only vents breathing gas to the environment from measurement chamber 4 via exhaust outlet 5, it also includes an additional outlet 13 in communication with inlet 11. This additional outlet can be used to supply the inflator/deflator of a buoyancy compensator.

Figure 4:
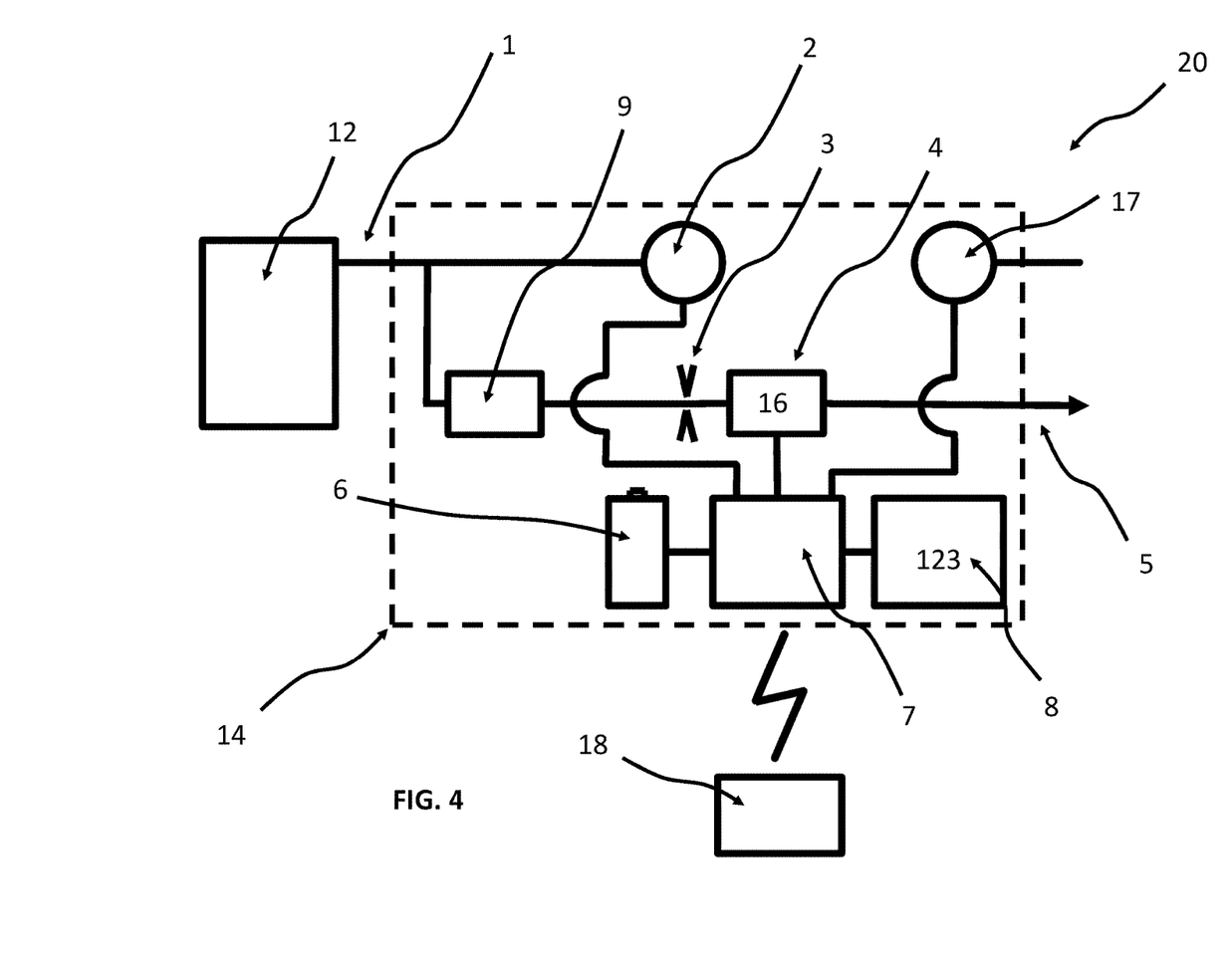
FIG. 4 is a schematic representation of an alternate configuration of the tank pressure transmitter with integrated breathing gas analyzer of FIG. 1.

FIG. 4 shows a configuration system 20 which is identical to the configuration of system 20 shown in FIG. 1 except that it includes a pressure regulator 9. Pressure regulator 9 reduces the pressure at inlet 1 to a constant absolute pressure upstream from orifice 3 and measurement chamber 4. This has the advantage of allowing a larger orifice 3 to be used which is easier and more cost efficient to manufacture and is less prone to clogging. Further this configuration can be designed so that the output pressure from pressure regulator 9 is only slightly higher than the surface pressure.

As example, assuming a surface pressure of 1 bar and that pressure regulator 9 is set to 1.5 bar pressure. On the surface the pressure at the inlet of orifice 3 is higher than the pressure at exhaust outlet 5, thus there is a gas flow through the orifice 3 to the measurement chamber 4 and the gas flow can be analyzed with gas sensor 16 in measurement chamber 4. However as soon as the diver descends below 5 m, the pressure at the exhaust outlet 5 becomes higher than the pressure at the inlet of orifice 3, thus there is no breathing gas flow anymore.

This is advantageous in terms of reducing waste breathing gas during the dive. It is sufficient to analyze the breathing gas on the surface, and therefore a breathing gas flow through the measurement chamber is not necessary at depth. Ideally in this arrangement the exhaust outlet 5 is also equipped with a directional valve, e.g. a check valve, in order to prevent water entry into measurement chamber 4 and orifice 3.

Figure 5:
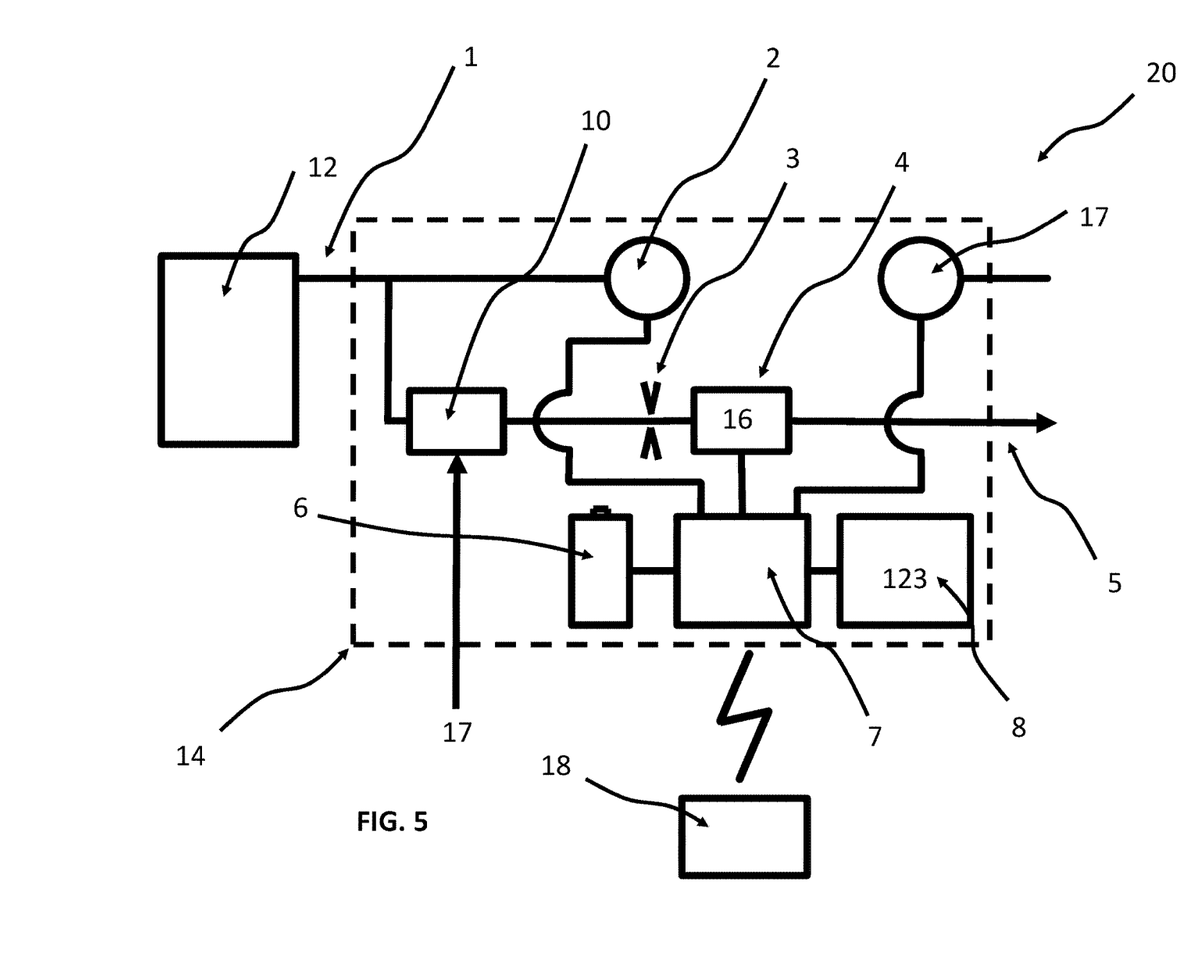
FIG. 5 is a schematic representation of an alternate configuration of the tank pressure transmitter with integrated breathing gas analyzer of FIG. 1.

Turning now to FIG. 5, the configuration shown therein is identical to the configuration of FIG. 4, except that it utilizes an ambient pressure compensated regulator 10, where the output pressure is constant above ambient pressure. Similar to the configuration shown in FIG. 4, this arrangement allows using an orifice 3 with a larger diameter. This regulator 10 may be independently connected via a conduit to ambient, or alternatively, may receive the same ambient pressure sent to ambient pressure sensor 17 introduced above.

In configuration of FIG. 5, there is always a gas flow through the orifice independent on depth. During a dive, the gas fractions of the breathing gas are usually constant. However as the ambient pressure increases during the dive with approximately 1 bar each 10 meters depth, the partial pressure of the constituents increase accordingly. Contemporary gas sensing technology is based on measurement of partial pressures rather than fractions, thus in the configuration shown in FIG. 5, the gas sensor 16 would measure different partial pressures dependent on the divers depth. If the illustrated ambient pressure sensor 10 is included, however, it is possible to validate or even auto-calibrate the gas sensor 16 during a dive as the ambient pressure at all times is factored in. Additionally, system 20 may utilize a wet sensor to detect when system 20 is submerged.

Figure 6:
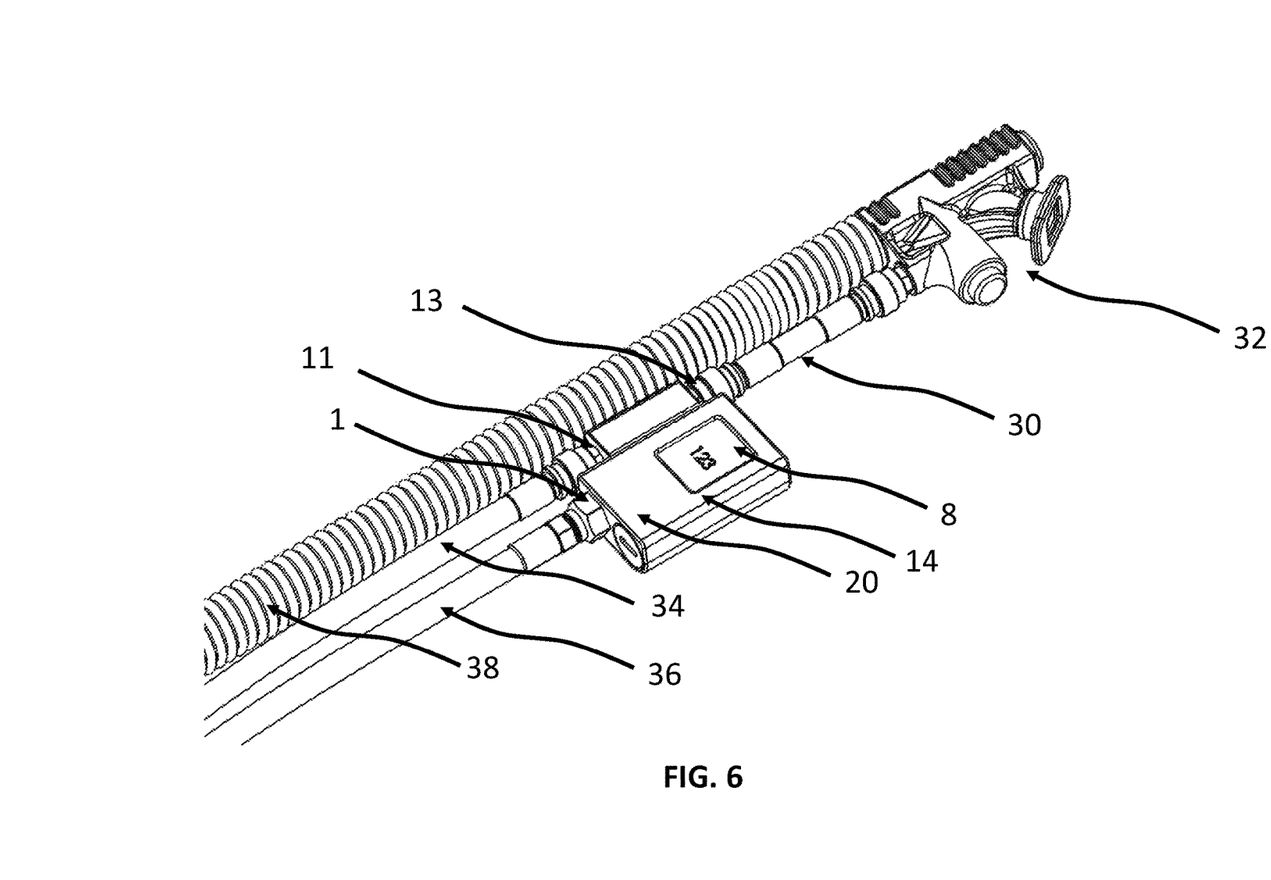
FIG. 6 is one exemplary embodiment of the tank pressure transmitter with integrated breathing gas analyzer integrated with a diving system, in particular, a buoyancy compensator.

FIG. 6 illustrates an exemplary physical embodiment of the system 20 herein. This embodiment is indicative of the dual inlet configurations of system 20 shown in FIGS. 2 and 3. In the illustrated embodiment, system 20 is installed in line with the breathing gas supply of a buoyancy compensator. As described above, system 20 is supplied with breathing gas through the intermediate pressure inlet 11 which is connected with an intermediate pressure hose 34 to an intermediate pressure port of a first stage pressure regulator.

The intermediate pressure outlet 13 is connected with another intermediate pressure hose 30 to the inflator/deflator 32, of a buoyancy compensator as is also schematically shown in FIG. 3. As is also described above, inlet 1 is connected to a high pressure hose 36 connected to the high pressure port of a first stage pressure regulator. As can be seen in this view, display 8 is conveniently arranged to display the pressure and constituent readings directly on housing 14.

Figure 7:
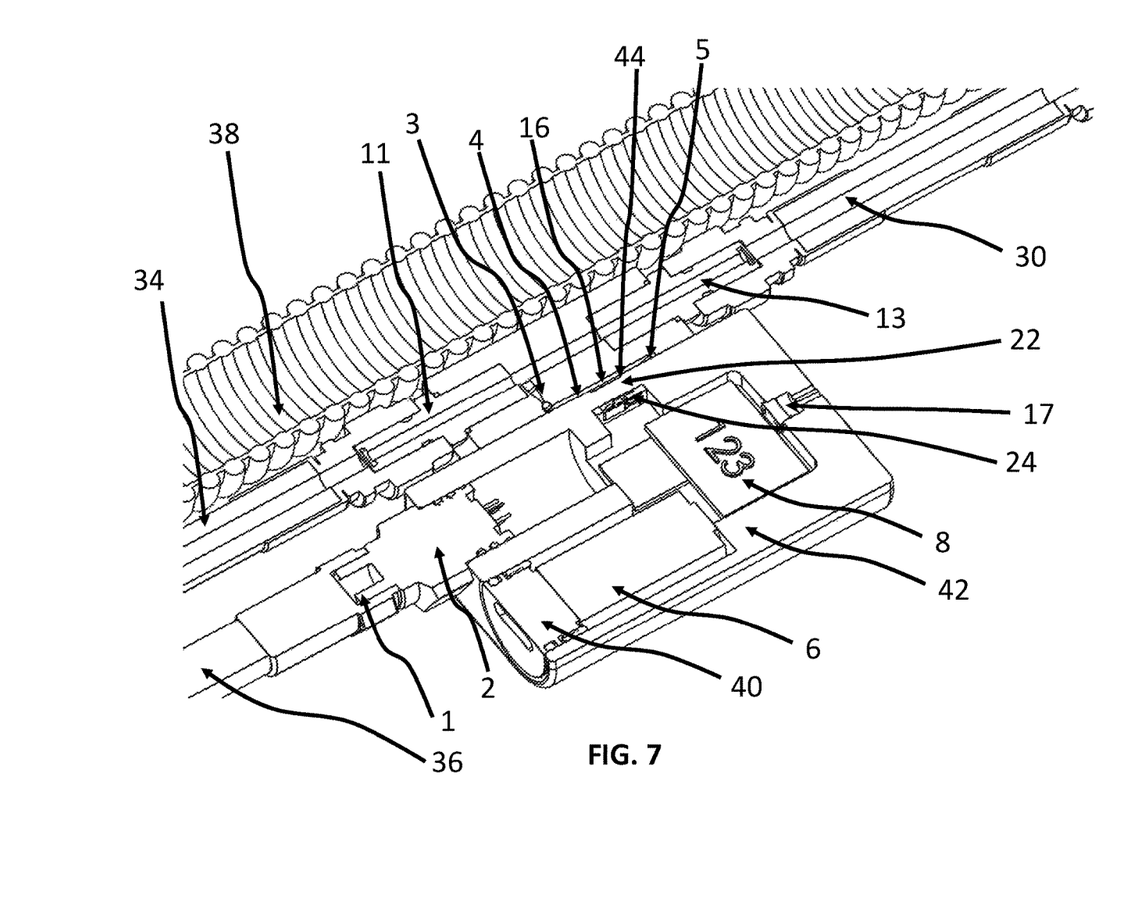
FIGS. 7 and 8 are cross sections of the embodiment of FIG. 6.

FIG. 7 is a cross section of the embodiment shown in FIG. 6. Pressure sensor 2 is fed with breathing gas through inlet 1 via high pressure supply hose 36. Intermediate pressure gas inlet 11 is connected with an intermediate pressure hose 34 to an intermediate pressure outlet of a first stage pressure regulator. The connection between gas inlet 11 and hose 34 may be permanent or configured so as to avoid inadvertent disconnection, as disconnection can lead to a false reading due to air entry, and/or the flooding of the chamber containing the gas sensor(s). Intermediate pressure outlet 13 is connected with an intermediate pressure hose 30 to an inflator/deflator of a buoyancy compensator. As can also be seen in this view, a number of seals are used at the various inlets 1, 11, and outlets 5, 12, to prevent the ingress of water into housing 14. Additionally, a gasket 42 may be utilized with housing 14 where housing 14 is formed of two joinable housing shells (not shown).

Orifice 3 is fed with breathing gas from the intermediate pressure inlet 11. The breathing gas flow through orifice 3 then travels into measurement chamber 4 where one or more gas sensors 16 are located. In the illustrated embodiment, a single gas sensor 16 is utilized. However, it is also possible to situate multiple gas sensors 16 within measurement chamber 4. Indeed, as one non-limiting example, it is possible to situate both a helium gas sensor as well as an oxygen gas sensor within measurement chamber 16. It is also possible to employ a single gas sensor 16 which is operable to detect multiple types of gas.

The breathing gas flow then exits through an exhaust outlet 5 after gas sensor 16 is exposed to the breathing gas. As stated above, a pressure regulator 9, 10 may be included upstream from orifice 3. Further, a uni-directional flow device such as a check valve 5 may also be used at exhaust outlet 5. As can also be seen in the FIG. 7, a battery cap 40 is also employed to secure battery 6 within housing 14.

The particular gas sensor 16 in FIG. 7 is an optical fluorescence based gas sensor, where the sensing membrane 44 is located in measurement chamber 4 and is in contact with breathing gas therein. An electronic circuit 24 of control arrangement 7 emits light through a transparent window 22 onto the sensing membrane 44, which causes color pigments in the membrane 44 to start fluorescing. The intensity of the fluorescence as well as the decay time of the fluorescence once the membrane is not illuminated depends on the partial pressure of the constituent. This fluorescence is detected by circuit 24, e.g. by a light sensor, and is then communicated to the remainder of control arrangement 7.

Figure 8:
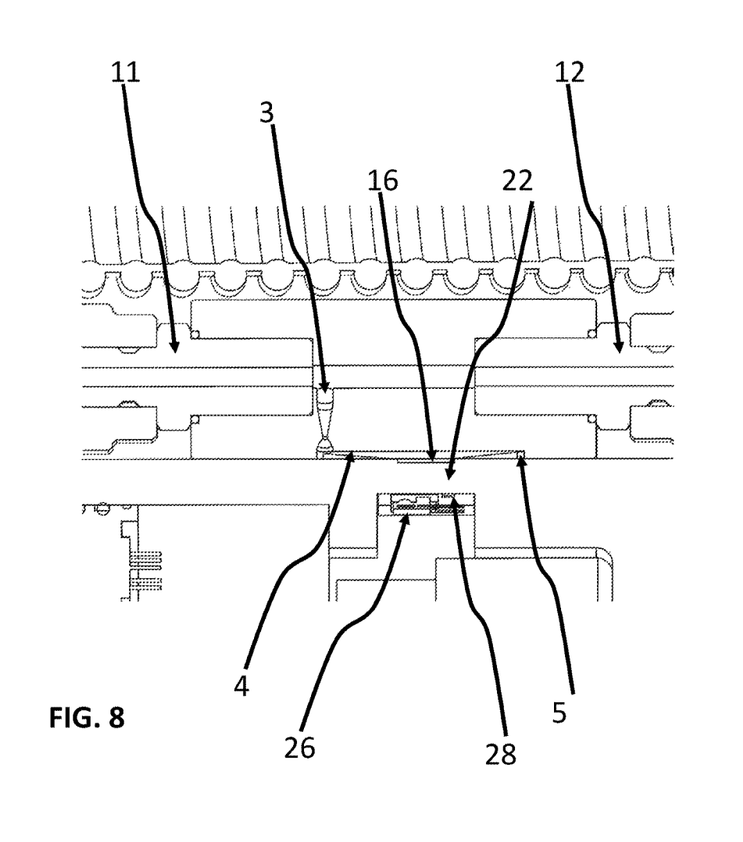

FIG. 8 shows an enlarged section of the cross section of FIG. 7. Sensing membrane 44 is illuminated with a suitable light source 28 of circuit 24 through transparent window 22. The fluoresced light is analyzed with one or more light receivers 26 and optical filters which can be located in front of the receiver of also be integrated into the receiver.

Figure 9:
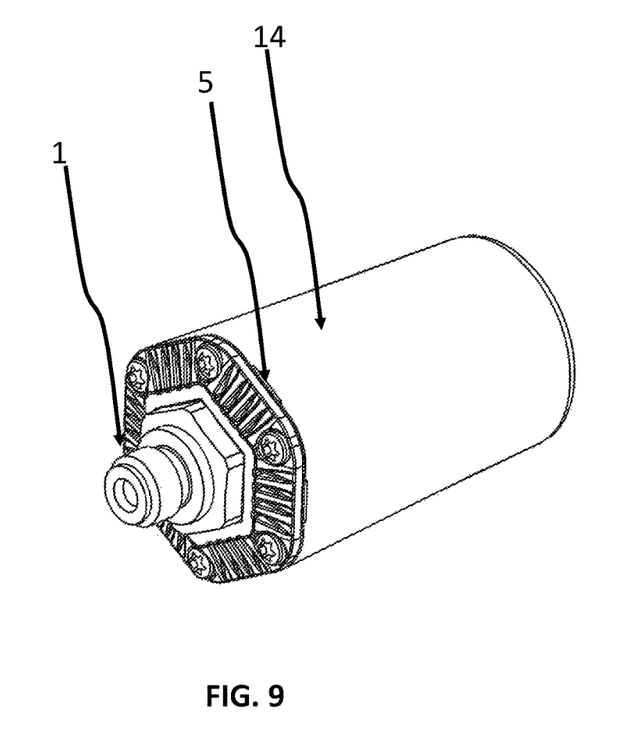
FIG. 9 is an alternative embodiment of the tank pressure transmitter with integrated breathing gas analyzer.

FIG. 9 shows an example of a physical embodiment of a single inlet configuration such as that schematically shown in FIGS. 4 and 5. Inlet 1 is connected to a high pressure outlet of a first stage pressure regulator. Breathing gas is conveyed to the measurement chamber 4. This breathing gas is then conveyed from the measurement chamber 4 is vented into the environment through an exhaust outlet (5). Housing 14 is typically made from plastics, to enable a wireless electromagnetic transmission to a dive computer.

All references, including publications, patent applications, and patents cited herein are hereby incorporated by reference to the same extent as if each reference were individually and specifically indicated to be incorporated by reference and were set forth in its entirety herein.

The use of the terms "a" and "an" and "the" and similar referents in the context of describing the invention (especially in the context of the following claims) is to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

What is claimed is:

1. A wireless tank pressure transmitter, comprising:
   a housing having at least one inlet, the at least one inlet operable to receive an inlet flow of breathing gas from a high pressure regulator;
   a pressure sensor disposed within the housing and connected to the at least one inlet and operable to detect a pressure of the breathing gas supplied through the at least one inlet;
   a gas sensor disposed within the housing and connected to the at least one inlet and operable to detect a constituent of the breathing gas;
   a control arrangement disposed within the housing and configured for compiling a pressure reading from the pressure taken by the pressure sensor and for compiling a constituent reading from the constituent taken by the gas sensor;
   wherein the control arrangement is configured for wireless communication of the pressure reading and the constituent reading to a dive computer; and
   wherein the at least one inlet includes a high pressure inlet and an intermediate inlet, the high pressure inlet to be connected to a high pressure outlet port of the high pressure regulator, the intermediate inlet to be connected to an intermediate outlet port of the high pressure regulator.

2. The wireless tank pressure transmitter of claim 1, wherein the gas sensor is an oxygen sensor.

3. The wireless tank pressure transmitter of claim 2, wherein the oxygen sensor is one of an optical oxygen sensor, a galvanic oxygen sensor, a solid state ceramic oxygen sensor, and a paramagnetic oxygen sensor.

4. The wireless tank pressure transmitter of claim 1, wherein the gas sensor is disposed within a measurement chamber and the measurement chamber includes a vent for evacuating the breathing gas therefrom.

5. The wireless tank pressure transmitter of claim 1, wherein the gas sensor is disposed within a measurement chamber, and further comprising a pressure regulator disposed upstream from a flow orifice relative to the flow direction of the breathing gas, the flow orifice disposed upstream from the measurement chamber relative to the direction of flow of the breathing gas, the pressure regulator operable to regulate the pressure of the inlet flow of breathing gas to the measurement chamber.

6. The wireless tank pressure transmitter of claim 5, wherein the pressure regulator is an ambient pressure compensated pressure regulator.

7. The wireless tank pressure transmitter of claim 1, wherein the constituent reading is at least one of a fraction of oxygen in the breathing gas and a partial pressure of oxygen in the breathing gas.

8. The wireless tank pressure transmitter of claim 1, further comprising at least one additional gas sensor, wherein the gas sensor and at least one additional gas sensor are each configured to detect a different constituent from one another.

9. The wireless tank pressure transmitter of claim 8, wherein one of the gas sensor and the at least one additional gas sensor is a helium sensor.

10. The wireless tank pressure transmitter of claim 8, wherein one of the gas sensor and the at least one additional gas sensor is a carbon monoxide sensor.

11. The wireless tank pressure transmitter of claim 1, wherein a first flow of the breathing gas from the high pressure inlet is provided to the pressure sensor, and wherein a second flow of the breathing gas from the intermediate inlet is provided to the gas sensor.

\* \* \* \* \*